(12) United States Patent
Luengo et al.

(10) Patent No.: US 6,642,265 B1
(45) Date of Patent: Nov. 4, 2003

(54) THROMBOPOIETIN MIMETICS

(75) Inventors: Juan I. Luengo, Audubon, PA (US); Kevin J. Duffy, Norristown, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/070,702

(22) PCT Filed: Sep. 8, 2000

(86) PCT No.: PCT/US00/24665

§ 371 (c)(1),
(2), (4) Date: Mar. 8, 2002

(87) PCT Pub. No.: WO01/17349

PCT Pub. Date: Mar. 15, 2001

(51) Int. Cl.⁷ .................... A61K 31/415; C07D 213/18

(52) U.S. Cl. .................. 514/407; 514/150; 514/406; 548/374.1; 548/366.1

(58) Field of Search .................. 514/407; 548/366.1, 548/374.1

(56) References Cited

U.S. PATENT DOCUMENTS 5,482,546 A    1/1996   Eida

*Primary Examiner*—Dwayne C. Jones
(74) *Attorney, Agent, or Firm*—Wayne J. Dustman; Stephen Venetianer; Charles M. Kinzig

(57) ABSTRACT

Invented are non-peptide TPO mimetics. Also invented is a method of treating thrombocytopenia, in a mammal, including a human, in need thereof which comprises administering to such mammal an effective amount of a selected hydroxy-1-azobenzene derivative.

16 Claims, No Drawings

THROMBOPOIETIN MIMETICS

This application is a 371 of PCT/US00/24665, filed on Sep. 8, 2000.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitrotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538(1994). Thrombopoietin is a glycoprotein with at least two forms, with apparent molecular masses of 25 kDa and 31 kDa, with a common N-terminal amino acid sequence. See, Bartley, et al., *Cell* 77: 1117–1124 (1994). Thrombopoietin appears to have two distinct regions separated by a potential Arg-Arg cleavage site. The aminoterminal region is highly conserved in man and mouse, and has some homology with erythropoietin and interferon-a and interferon-b. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoietin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression if restricted to spleen, bone marrow, or fetal liver in mice (see Souyri et al. *Cell* 63: 1137–1147 (1990)) and to megakaryocytes, platelets, and CD34$^+$ cells in humans (see Methia et al. *Blood* 82: 1395–1401 (1993)). Further evidence for TPO-R as a key regulator of megakaryopoiesis is the fact that exposure of CD34$^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration.

It would be desirable to provide compounds which allow for the treatment of thrombocytopenia by acting as a TPO mimetic.

As disclosed herein it has unexpectedly been discovered that certain hydroxy-1-azo-benzene derivatives are effective as agonists of the TPO receptor, they are potent TPO mimetics.

SUMMARY OF THE INVENTION

This invention relates to compounds of Formula (I):

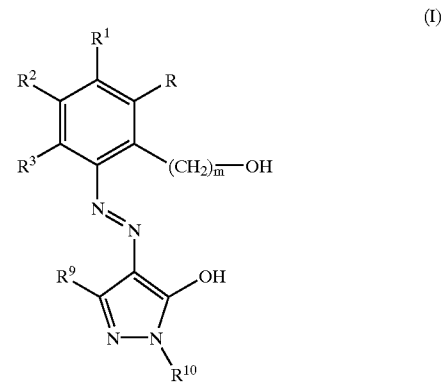

(I)

wherein
R, R$^1$, R$^2$, R$^3$ and R$^9$ are each independently selected from hydrogen, C$_{1-6}$alkyl, C$_{1-6}$alkoxy, —(CH$_2$)$_p$OR$^4$, —C(O)OR$^4$, nitro, cyano, halogen, aryl, —S(O)$_n$R$^4$, cycloalkyl, protected OH, —CONR$^5$R$^6$, phosphonic acid, sulfonic acid, phosphinic acid and —SO$_2$NR$^5$R$^6$, where p is 0–6;
n is 0–2;
R$^4$ is hydrogen, alkyl, cycloalkyl, C$_1$–C$_{12}$aryl, substituted alkyl, substituted cycloalkyl and substituted C$_1$–C$_{12}$aryl, and
R$^5$ and R$^6$ are each independently selected from hydrogen, alkyl, C$_{3-6}$cycloalkyl, and aryl,
or R$^5$ and R$^6$ taken together with the nitrogen to which they are attached represent a 5 to 6 member saturated ring containing up to one other heteroatom selected from oxygen and nitrogen;
m is 0–6; and
R$^{10}$ is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, cycloalkyl, substituted cycloalkyl, aryl, substituted aryl, aryloxy, alkoxy, acyloxy, amino, nitro, cyano, halogen, hydroxy, protected —OH, and alkyl substituted with one or more substituents selected from the group consisting of: alkoxy, acyloxy, aryl, substituted aryl, cycloalkyl, substituted cycloalkyl, aryloxy, amino, nitro, cyano, halogen, hydroxy, and protected —OH; and
pharmaceutically acceptable salts, hydrates, solvates and esters thereof;
provided that:
at least one of R, R$^1$, R$^2$ and R$^3$ is: sulfonic acid, —C(O)OR$^4$, tetrazole, —CONR$^5$R$^6$, phosphonic acid or phosphinic acid; where R$^4$, R$^5$ and R$^6$ are as described above;
and provided that:
when R$^1$ is carboxylic acid; R, R$^2$ and R$^3$ are hydrogen; and R$^9$ is methyl;
R$^{10}$ is not unsubstituted phenyl.

This invention relates to a method of treating thrombocytopenia, which comprises administering to a subject in need thereof an effective amount of a TPO mimetic compound of Formula (II):

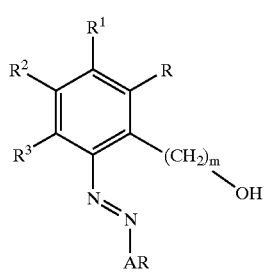

(II)

wherein:
R, R$^1$, R$^2$ and R$^3$ are each independently selected from hydrogen, C$_{1-6}$alkyl, C$_{1-6}$alkoxy, —(CH$_2$)$_p$OR$^4$, —C(O)OR$^4$, nitro, cyano, halogen, aryl, —S(O)$_n$R$^4$, cycloalkyl, protected —OH, —CONR$^5$R$^6$, —NR$^5$R$^6$, phosphonic acid, sulfonic acid, phosphinic acid and —SO$_2$NR$^5$R$^6$, where p is 0–6;
n is 0–2;
R$^4$ is hydrogen, alkyl, cycloalkyl, C$_1$–C$_2$aryl, substituted alkyl, substituted cycloalkyl and substituted C$_1$–C$_{12}$aryl and
R$^5$ and R$^6$ are each independently selected from hydrogen, alkyl, C$_{3-6}$cycloalkyl, and aryl,
or R$^5$ and R$^6$ taken together with the nitrogen to which they are attached represent a 5 to 6 member saturated ring containing up to one other heteroatom selected from oxygen and nitrogen;
m is 0–6; and
AR is cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, aryl, substituted cycloalkyl, substituted aryl, aryloxy, hydroxy, alkoxy, cycloalkyl, acyloxy, amino, N-acylamino, nitro, cyano, halogen, —C(O)OR$^4$, —C(O)NR$^7$R$^8$, —S(O)$_2$NR$^7$R$^8$, —S(O)$_n$R$^4$, protected —OH and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR$^4$, —C(O)NR$^7$R$^8$, —S(O)$_2$NR$^7$R$^8$, —S(O)$_n$R$^4$, aryloxy, nitro, cyano, halogen, and protected —OH, where
R$^4$ is hydrogen, alkyl, cycloalkyl, C$_1$–C$_{12}$aryl, substituted alkyl, substituted cycloalkyl and substituted C$_1$–C$_{12}$aryl; and
R$^7$ and R$^8$ are independently hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, C$_1$–C$_{12}$aryl, substituted C$_1$–C$_{12}$aryl and protected —OH,
or R$^7$ and R$^8$ taken together with the nitrogen to which they are attached represent a 5 to 6 member saturated ring containing up to one other heteroatom selected from oxygen and nitrogen,
where R$^4$ is as described above and n is 0–2; and
pharmaceutically acceptable salts, hydrates, solvates and esters thereof.

The present invention also relates to the discovery that the compounds of Formula (II) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

The presently invented compounds that act as TPO mimetics are defined by Formula (I) above.

Preferred among the presently invented Formula I compounds are those in which $R^1$ is carboxylic acid or sulfonic acid; R, $R^2$ and $R^3$ are each independently selected from hydrogen, carboxylic acid, $C_1$–$C_{12}$aryl, sulfonic acid, tetrazole, —$CONR^5R^6$ where $R^5$ and $R^6$ are as described in Formula I above, phosphonic acid, phosphinic acid, $C_{1-6}$alkoxy, nitro, $C_{1-6}$alkyl and halogen; m is 0; $R^9$ is $C_{1-6}$alkyl, $C_{1-6}$alkoxy, halogen, or $C_1$–$C_{12}$aryl; and $R^{10}$ is a cyclic or polycyclic aromatic ring containing from 3 to 14 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, $C_1$–$C_{12}$aryl, substituted cycloalkyl, substituted $C_1$–$C_{12}$aryl, aryloxy, alkoxy, trifluoromethyl, cycloalkyl, nitro, cyano, hydroxy, halogen and protected —OH; and pharmaceutically acceptable salts, hydrates, solvates and esters thereof.

Particularly preferred among the presently invented Formula I compounds are those in which $R^1$ is carboxylic acid or sulfonic acid; R, $R^2$ and $R^3$ are each independently elected from hydrogen, $C_{1-6}$alkoxy, tetrazole, —$CONR^5R^6$ where $R^5$ and $R^6$ are as described in Formula I above, phosphonic acid, phosphinic acid, $C_{1-6}$alkyl and halogen; m is 0; $R^9$ is $C_{1-6}$alkyl, $C_{1-6}$alkoxy, halogen, or $C_1$–$C_{12}$aryl; and $R^{10}$ is phenyl substituted with one or more substituents selected from the group consisting of: alkyl, substituted alkyl, alkoxy, trifluoromethyl, halogen, hydroxy and protected —OH; and pharmaceutically acceptable salts, hydrates, solvates and esters thereof.

The most preferred among the presently invented Formula I compounds are those in which $R^1$ is carboxylic acid or sulfonic acid; R, $R^2$ and $R^3$ are each independently selected from hydrogen, $C_{1-6}$alkoxy, $C_{1-6}$alkyl and halogen; m is 0; $R^9$ is $C_{1-6}$alkyl or $C_{1-6}$alkoxy and $R^{10}$ is phenyl substituted with from one to three substituents selected from the group consisting of: alkyl, hydroxy, alkoxy, trifluoromethyl and halogen; and pharmaceutically acceptable salts, hydrates, solvates and esters thereof.

Preferred among the presently invented compounds of Formula I are 3-hydroxy-4-{[5-hydroxy-3-methyl-1-(4-methylphenyl)-1H-pyrazol-4-yl]azo}benzoic acid;

4-{[1-(4-benzyloxyphenyl)-5-hydroxy-3-methyl-1H-pyrazol-4-yl]azo}-3-hydroxybenzoic acid;

4-{[1-(4-chlorophenyl)-5-hydroxy-3-methyl-1H-pyrazol-4-yl]azo}-3-hydroxybenzoic acid;

4-{[1-(3-chlorophenyl)-5-hydroxy-3-methyl-1H-pyrazol-4-yl]azo}-3-hydroxybenzoic acid;

4-{[1-(3,4-dimethylphenyl)-5-hydroxy-3-methyl-1H-pyrazol-4-yl]azo}-3-hydroxybenzoic acid;

3-{[1-(3,4-dimethylphenyl)-5-hydroxy-3-methyl-1H-pyrazol-4-yl]azo}-4-hydroxybenzoic acid;

3-hydroxy-4-{[5-hydroxy-3-methyl-1-(3-methylphenyl)-1H-pyrazol-4-yl]azo}benzoic acid;

3-hydroxy-4-{[5-hydroxy-3-methyl-1-(4-trifluoromethylphenyl)-1H-pyrazol-4-yl]azo}benzoic acid;

3-{[1-(3,4-dimethylphenyl)-5-hydroxy-3-methyl-1H-pyrazol-4-yl]azo}-2-hydroxybenzoic acid;

2-{[1-(3,4-dimethylphenyl)-5-hydroxy-3-methyl-1H-pyrazol-4-yl]azo}-3-hydroxybenzoic acid;

5-chloro-3-{[1-(3,4-dimethylphenyl)-5-hydroxy-3-methyl-1H-pyrazol-4-yl]azo}-2-hydroxybenzenesulfonic acid;

3-tert-butyl-4-{[1-(3,4-dimethylphenyl)-5-hydroxy-1H-pyrazol-4-yl]azo}-3-hydroxybenzoic acid;

4-{[1-(3,4-dimethylphenyl)-5-hydroxy-3-phenyl-1H-pyrazol-4-yl]azo}-3-hydroxybenzoic acid;

methyl 3-hydroxy-4-{[5-hydroxy-3-methyl-1-(4-methylphenyl)-1H-pyrazol-4-yl]azo}benzoate; and 4-{[1-(4-tert-butylphenyl)-5-hydroxy-3-methyl-1H-pyrazol-4-yl]azo}-3-hydroxybenzoic acid;

and pharmaceutically acceptable salts, hydrates, solvates and esters thereof.

This invention relates to a method of treating thrombocytopenia, which comprises administering to a subject in need thereof an effective amount of a TPO mimetic compound defined by Formula (II) above.

Preferred among the compounds of Formula II are those in which $R^1$ is carboxylic acid or sulfonic acid; R, $R^2$ and $R^3$ are each independently selected from hydrogen, carboxylic acid, $C_1$–$C_{12}$aryl, sulfonic acid, tetrazole, —$CONR^5R^6$ where $R^5$ and $R^6$ are as described in Formula II above, phosphonic acid, phosphinic acid, $C_{1-6}$alkoxy, nitro, $C_{1-6}$alkyl and halogen; m is 0; and AR is a cyclic or polycyclic aromatic ring containing from 3 to 14 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, $C_1$–$C_{12}$ aryl, substituted cycloalkyl, substituted $C_1$–$C_{12}$aryl, aryloxy, hydroxy, alkoxy, cycloalkyl, amino, nitro, cyano, halogen and protected —OH; and pharmaceutically acceptable salts, hydrates, solvates and esters thereof.

Particularly preferred among the compounds of Formula II are those in which $R^1$ is carboxylic acid or sulfonic acid; R, $R^2$ and $R^3$ are each independently selected from hydrogen, $C_{1-6}$alkoxy, tetrazole, —$CONR^5R^6$ where $R^5$ and $R^6$ are as described in Formula II above, phosphonic acid, phosphinic acid, $C_{1-6}$alkyl and halogen; m is 0; and AR is a cyclic or polycyclic aromatic ring containing from 3 to 14 carbon atoms, optionally containing one or more heteroatoms, provided that when the number of carbon atoms is 3 the aromatic ring contains at least two heteroatoms and when the number of carbon atoms is 4 the aromatic ring at least one heteroatom, and optionally substituted with one or more substituents selected from the group consisting of: alkyl, $C_1$–$C_{12}$ aryl, substituted $C_1$–$C_{12}$aryl, aryloxy, hydroxy, alkoxy, amino, halogen and protected —OH; and pharmaceutically acceptable salts, hydrates, solvates and esters thereof.

The most preferred among the compounds of Formula II are those in which $R^1$ is carboxylic acid or sulfonic acid; R, $R^2$ and $R^3$ are each independently selected from hydrogen, $C_{1-6}$alkoxy, $C_{1-6}$alkyl and halogen; m is 0; and AR is selected from naphthalene, phenyl and pyrazole, and optionally substituted with from one to three substituents selected from the group consisting of: alkyl, $C_1$–$C_{12}$ aryl, substituted $C_1$–$C_{12}$aryl, hydroxy, alkoxy and halogen; and pharmaceutically acceptable salts, hydrates, solvates and esters thereof.

Preferred among the compounds of Formula II are 3-hydroxy-4-{[5-hydroxy-3-methyl-1-(4-methylphenyl)-1H-pyrazol-4-yl]azo}benzoic acid;

3-hydroxy-4-[(5-hydroxy-3-methyl-1-phenyl-1H-pyrazol-4-yl)azo]benzoic acid;

4-{[1-(4-benzyloxyphenyl)-5-hydroxy-3-methyl-1H-pyrazol-4-yl]azo}-3-hydroxybenzoic acid;

4-{[1-(4-chlorophenyl)-5-hydroxy-3-methyl-1H-pyrazol-4-yl]azo}-3-hydroxybenzoic acid;

4-{[1-(3-chlorophenyl)-5-hydroxy-3-methyl-1H-pyrazol-4-yl]azo}-3-hydroxybenzoic acid;

4-{[1-(3,4-dimethylphenyl)-5-hydroxy-3-methyl-1H-pyrazol-4yl]azo}-3-hydroxybenzoic acid;

3-{[1-(3,4-dimethylphenyl)-5-hydroxy-3-methyl-1H-pyrazol-4-yl]azo}4-hydroxybenzoic acid;

3-hydroxy-4-{[5-hydroxy-3-methyl-1-(3-methylphenyl)-1H-pyrazol-4-yl]azo}benzoic acid;

3-hydroxy-4-{[5-hydroxy-3-methyl-1-(4-trifluoromethylphenyl)-1H-pyrazol-4-yl]azo}benzoic acid;

3-{[1-(3,4-dimethylphenyl)-5-hydroxy-3-methyl-1H-pyrazol-4-yl]azo}-2-hydroxybenzoic acid;

2-{[1-(3,4-dimethylphenyl)-5-hydroxy-3-methyl-1H-pyrazol-4-yl]azo}-3-hydroxybenzoic acid;

5-chloro-3-{[1-(3,4-dimethylphenyl)-5-hydroxy-3-methyl-1H-pyrazol-4-yl]azo}-2-hydroxybenzenesulfonic acid;

3-tert-butyl-4-{[1-(3,4-dimethylphenyl)-5-hydroxy-1H-pyrazol-4-yl]azo}-3-hydroxybenzoic acid;

4-{[1-(3,4-dimethylphenyl)-5-hydroxy-3-phenyl-1H-pyrazol-4-yl]azo}-3-hydroxybenzoic acid;

methyl 3-hydroxy-4-{[5-hydroxy-3-methyl-1-(4-methylphenyl)-1H-pyrazol-4-yl]azo}benzoate; and 4-{[1-(4-tert-butylphenyl)-5-hydroxy-3-methyl-1H-pyrazol-4-yl]azo}-3-hydroxybenzoic acid;

and pharmaceutically acceptable salts, hydrates, solvates and esters thereof.

Compounds of Formula (I) are included in the pharmaceutical compositions of the invention and used in the methods of the invention.

Compounds of Formula (II) are included in the pharmaceutical compositions of the invention and used in the methods of the invention.

By the term "protected hydroxy" or "protected —OH" as used herein, is meant the alcoholic or carboxylic —OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbon atoms is 3 the aromatic ring contains at least two heteroatoms and when the number of carbon atoms is 4 the aromatic ring contains at least one heteroatom.

By the term "$C_1$–$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —$(CH_2)_gC(O)OR^{11}$, —$S(O)_nR^{12}$, nitro, cyano, halogen, trifluoromethyl and protected —OH, where g is 0–6, $R^{11}$ is hydrogen or alkyl, n is 0–2, and $R^{12}$ is hydrogen or alkyl.

By the term "alkoxy" as used herein is meant -Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —$N(H)C(O)$alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$–$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^{11}$, —$S(O)_nR^{12}$, nitro, cyano, halogen and protected —OH, where g is 0–6, $R^{11}$ is hydrogen or alkyl, n is 0–2 and $R^{12}$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$, —$CH(CH_3)$—$CH_2$—$CH_3$, —$CH=CH_2$, and —$C\equiv C$—$CH_3$.

By the term "treating" and derivatives thereof as used herein, is meant prophylatic or therapeutic therapy.

All publications, including but not limited to patents and patent applications, cited in this specification are herein incorporated by reference as though fully set forth.

Compounds of Formula (II) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The novel compounds of Formula II are prepared as shown in Schemes I and II below, or by analogous methods, wherein R, $R^1$, $R^2$, $R^3$, AR and m are as defined in Formula I and provided that the 'R' and m substituents and AR do not include any such substituents that render inoperative the processes of Schemes I and II. All of the starting materials are commercially available or are readily made from commercially available starting materials by those of skill in the art.

Scheme I

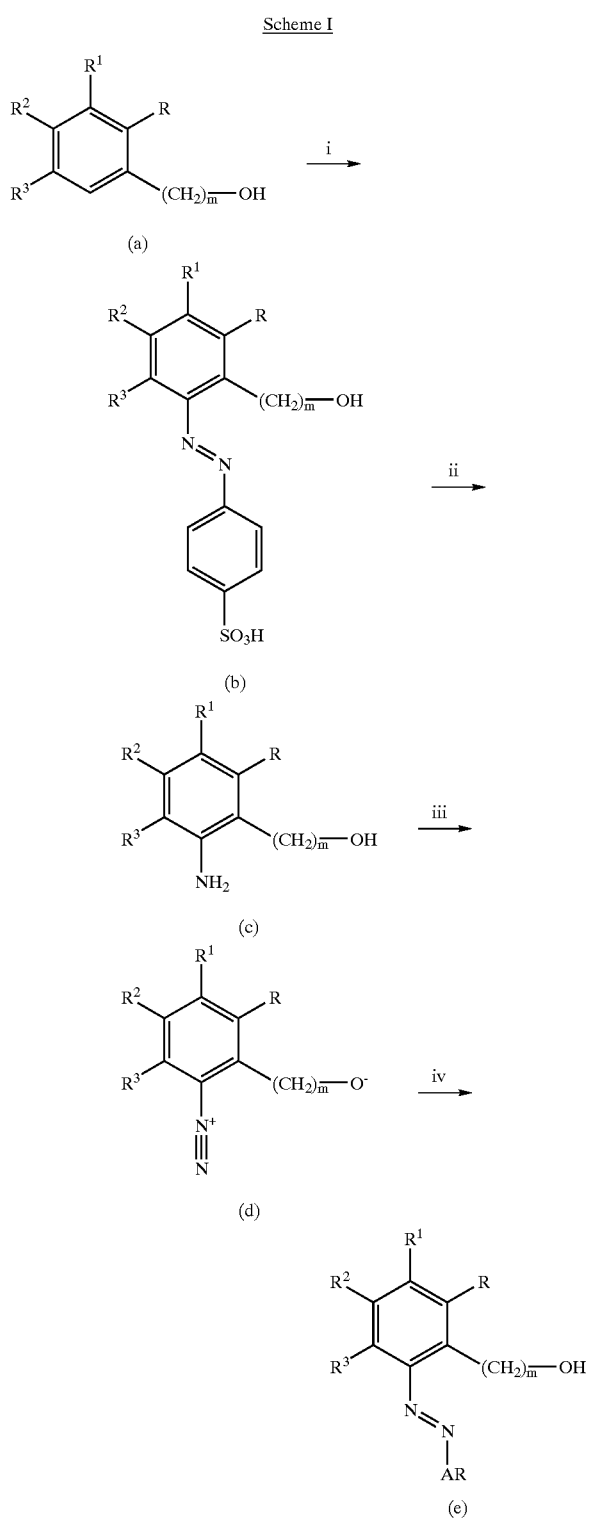

i) 4-amino-1-benzenesulfonic acid, NaNO₂, NaHCO₃, water; ii) NaHSO₃, water; iii) NaNO₂, HCl, water; iv) AR, NaHCO₃, water.

Scheme I outlines the formation of Formula II compounds. As used in scheme I the diazo compound (b) is prepared from the three hydroxybenzene compound (a) by treating (a) with 4-benzenediazonium sulfate in the presence of an appropriate base, preferably sodium hydrogen carbonate. Reduction of compound (b) with sodium hydrogen sulfite in water yielded the 2-aminohydroxybenzene compound (c). Compound (c) is diazotized by reaction with sodium nitrite and an appropriate acid, such as nitric acid, sulfuric acid or, preferably hydrochloric acid, in an appropriate aqueous solvent, such as water or, preferably an ethanol-water mixture to produce diazonium compound (d). Compound (e) is prepared by reacting compound (d) in a coupling reaction with an appropriate aryl species in the presence of a base, preferably sodium hydrogen carbonate, or an acid, preferably hydrochloric acid.

Scheme II

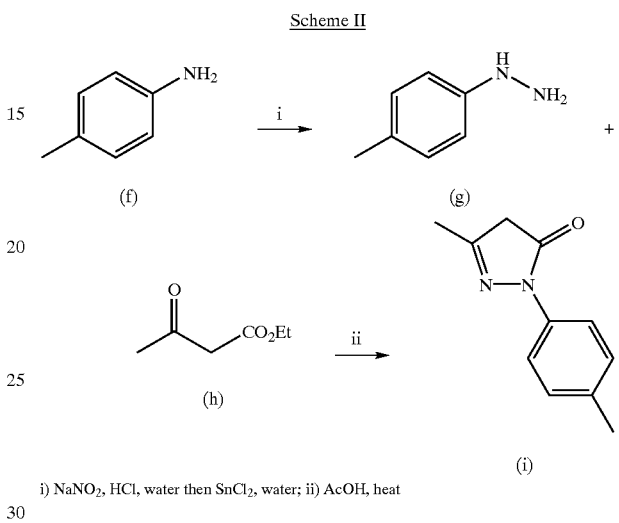

i) NaNO₂, HCl, water then SnCl₂, water; ii) AcOH, heat

Scheme II outlines the formation of pyrazoles for use in scheme I. An amine such as 4-methylaniline, compound (f), is diazotized by the action of sodium nitrite and an appropriate acid such as hydrochloric acid, nitric acid or sulfuric acid in an appropriate aqueous solvent system such as water or ethanol-water mixtures then reduced in situ by tin chloride to afford hydrazine, compound (g). The hydrazine is then condensed with a beta-keto ester such as ethyl acetoacetate, compound (h), in an appropriate solvent such as acetic acid or ethanol at an appropriate temperature typically 0–100° to give the corresponding pyrazole, compound (I) as described herein.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci. USA* 92: 3041–3045 (1995) by substituting a TPO-responsive BaF3 cell line (Vigon et a). *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells.

Some of the most preferred compounds of this invention were also active in an in vitro proliferation assay using the murine 32D-mpl cell line (Bartley, T. D. et al., Cell, 1994, 77, 1117–1124). 32D-mpl cells express Tpo-R and their survival is dependent on the presence of TPO. Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al Science, 1997, 276, 1696–1699).

The pharmaceutically active compounds within the scope of this invention are useful as TPO mimetics in mammals, including humans, in need thereof.

Some of the preferred compounds within the scope of the invention showed activation from about 4% to 100% control at a concentration of 0.1–10 uM in the luciferase assay. The preferred compounds of the invention also promoted the proliferation of 32D-mpl cells at a concentration of 0.1 to 100 uM. The preferred compounds of the invention also showed activity in the CD41 megakaryocytic assay at a concentration of 0.1 to 30 uM.

The present invention therefore provides a method of treating thrombocytopenia and other conditions with depressed platelet production, which comprises administering a compound of Formula (II), as defined above, and pharmaceutically acceptable salts, hydrates, solvates and esters thereof, in a quantity effective to enhance platelet production. The compounds of Formula (E) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (II) in the manufacture of a medicament for use as a TPO mimetic.

The invention also provides for the use of a compound of Formula (II) in the manufacture of a medicament for use in therapy.

The invention also provides for the use of a compound of Formula (II) in the manufacture of a medicament for use in enhancing platelet production.

The invention also provides for the use of a compound of Formula (II) in the manufacture of a medicament for use in treating thrombocytopenia.

The invention also provides for a pharmaceutical composition for use as a TPO mimetic which comprises a compound of Formula (II) and a pharmaceutically acceptable carrier.

The invention also provides for a pharmaceutical composition for use in the treatment of thrombocytopenia which comprises a compound of Formula (II) and a pharmaceutically acceptable carrier.

The invention also provides for a pharmaceutical composition for use in enhancing platelet production which comprises a compound of Formula (II) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents—It will be appreciated by the person of ordinary skill in the art that the compounds of Formula I and II may also exist in tautomeric forms, wherein the double bond that is drawn between the two nitrogen atoms exists between the lower nitrogen atom and the AR substituent. Tautomeric forms of the compounds of Formula I and II are exemplified by the following Formula III

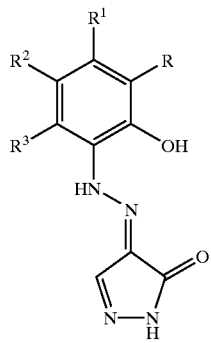

(III)

where the 'R' groups are as defined above. All such compounds are included in the scope of the invention and inherently included in the definition of the compounds of Formulas I and II.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

EXAMPLE 1

Preparation of 3-Hydroxy-4-{[5-hydroxy-3-methyl-1-(4-methylphenyl)-1H-pyrazol-4-yl]azo}benzoic Acid A solution of 4-amino-3-hydroxybenzoic acid (0.77 g, 0.005 mol.) in 1N aqu. hydrochloric acid (15.0 mL) was cooled to 0° C. and treated slowly with a solution of sodium nitrite (0.38 g; 0.0055 mol.) in water (5.0 mL). After addition the solution was stirred at 0° C. for 10 min. then 3-methyl-1-(4-methylphenyl)-3-pyrazolin-5-one (0.94 g; 0.005 mol.) was added in one portion. Ethanol (15.0 mL) was added followed by sat. aqu. sodium hydrogen carbonate until the pH of the solution was 8 (ca. 10 mL needed). The red solution was then stirred at room temperature for 16 h.

The mixture was filtered and the solid dissolved in 10% aqu. sodium hydroxide (50.0 mL). The red solution was extracted twice with ethyl acetate then acidified with 6N aqu. hydrochloric acid and filtered to give the title compound as a red solid (1.67 g; 95%). MS(ES) m/z 351 [M–H].

EXAMPLE 2

Preparation of 3-Hydroxy-4-[(5-hydroxy-3-methyl-1-phenyl-1H-pyrazol-4-yl)azo]benzoic Acid Following the procedure of Example 1, except substituting 3-methyl-1-phenyl-3-pyrazolin-5-one for 3-methyl-1-(4-methylphenyl)-3-pyrazolin-5-one, the title compound was prepared as a red solid. MS(ES) m/z 351 [M–H].

EXAMPLE 3

Preparation of 4-{[1-(4-Benzyloxyphenyl)-5-hydroxy-3-methyl-1H-pyrazol-4-yl]azo}-3-hydroxybenzoic Acid a) 4-Benzyloxyphenylhydrazine A solution of 4-benzyloxyaniline hydrochloride (11.3 g; 0.048 mole) in concentrated hydrochloric acid (40.0 mL) was cooled to 0° then treated dropwise with a solution of sodium nitrite (3.28 g; 0.048 mole) in water (20.0 mL). The mixture was stirred at 0° for a further 10 min. then poured into a cold (–10°) solution of tin dichloride hydrate (40.0 g; 0.18 mole) in concentrated hydrochloric acid (40.0 mL). The mixture was allowed to warm to room temperature with stirring for 1 h.

The mixture was basified with 10% aqu. sodium hydroxide, ethyl acetate (1L) was added and the mixture filtered to remove unwanted tin residues. The organic layer was then dried and evaporated to afford the title compound as a yellow solid (6.9 g; 67%). mp 105–107°.

b) 1-(4-Benzyloxyphenyl)-3-methyl-3-pyrazolin-5-one

A solution of the compound from Example 3a) (2.6 g; 0.012 mol.) and ethyl acetoacetate (1.60 mL; 0.012 mol.) in glacial acetic acid (50.0 mL) was stirred and heated at 100° for 24 h.

The solvent was evaporated and the product purified by chromatography (silica gel, 50% ethyl acetate/hexanes), the title compound was prepared (2.0 g; 60%). MS(ES) m/z 281 [M+H].

c) 4-{[1-(4-Benzyloxyphenyl)-5-hydroxy-3-methyl-1H-pyrazol-4-yl]azo}-3-hydroxybenzoic Acid Following the procedure of Example 1, except substituting 1-(4-benzyloxyphenyl)-3-methyl-3-pyrazolin-5-one for 3-methyl-1-(4-methylphenyl)-3-pyrazolin-5-one, and followed by chromatography (silica gel, 10% methanol/ethyl acetate), the title compound was prepared as a brown powder (19%). mp=258–260° C. (decomp).Anal. ($C_{24}H_{20}N_4O_5 \cdot CH_3OH$) calcd: C, 63.00; H, 5.08; N, 11.76 found: C, 63.17; H, 4.64; N, 11.47.

EXAMPLE 4

Preparation of 4-{[1-(4-Chlorophenyl)-5-hydroxy-3-methyl-1H-pyrazol-4-yl]azo}-3-hydroxybenzoic Acid Following the procedure of Example 1, except substituting 1-(4-chlorophenyl)-3-methyl-3-pyrazolin-5-one for 3-methyl-1-(4-methylphenyl)3-pyrazolin-5-one, the title compound was prepared as a red solid. MS(ES) m/z 371, 373 [M–H].

EXAMPLE 5

Preparation of 4-{[1-(3-Chlorophenyl)-5-hydroxy-3-methyl-1H-pyrazol-4-yl]azo}-3-hydroxybenzoic Acid Following the procedure of Example 1, except substituting 1-(3-chlorophenyl)-3-methyl-3-pyrazolin-5-one for 3-methyl-1-(4-methylphenyl)-3-pyrazolin-5-one, the title compound was prepared as a red solid. MS(ES) m/z 371, 373 [M–H].

EXAMPLE 6

Preparation of 4-{[1-(3,4-Dimethylphenyl)-5-hydroxy-3-methyl-1H-pyrazol-4-yl]azo}-3-hydroxybenzoic Acid a) 1-(3,4-Dimethylphenyl)-3-phenyl-3-pyrazolin-5-one Following the procedure of Example 3b), except substituting 3,4-dimethylphenylhydrazine for 4-benzyloxyphenylhydrazine, the title compound was prepared (16.0 g; 61%). MS(ES) m/z 265 [M+H].

b) 4-{[1-(3,4-Dimethylphenyl)-5-hydroxy-3-methyl-1H-pyrazol-4-yl]azo}-3-hydroxybenzoic Acid Following the procedure of Example 1, except substituting 1-(3,4-dimethylphenyl)-3-methyl-3-pyrazolin-5-one for 3-methyl-1-(4-methylphenyl)-3-pyrazolin-5-one, the title compound was prepared as an orange solid (1.5 g, 82%). $^1$H NMR (400 MHz, d6-DMSO) δ 13.5 br s, 1H), 11.0 (s, 1H), 7.70 (m, 2H), 7.61 (dd, J=8.2 and 2.1 Hz, 1H), 7.53 (m, 2), 8.20 (d, J=8.2 Hz, 1H), 2.30 (s, 3H), 2.27 (s, 3H), 2.22 (s, 3H).

EXAMPLE 7

Preparation of 3-{[1-(3,4-Dimethylphenyl)-5-hydroxy-3-methyl-1H-pyrazol-4-yl]azo}-4-hydroxybenzoic Acid Following the procedure of Example 1, except substituting 1-(3,4-dimethylphenyl)-3-methyl-3-pyrazolin-5-one for 3-methyl-1-(4-methylphenyl)-3-pyrazolin-5-one and 3-amino-4-hydroxybenzoic acid for 4-amino-3-hydroxybenzoic acid, the title compound was prepared as an orange solid (1.5 g, 82%). $^1$H NMR (400 MHz, d6-DMSO) δ 13.5 br s, 1H), 11.7 (s, 1H), 8.13 (d, J=2.0 Hz, 1H), 7.69–7.59 (m, 3H), 7.17 (d, J=8.4 Hz, 1H), 7.10 (d, J=8.5 Hz, 1H), 2.30 (s, 3H), 2.25 (s, 3H), 2.20 (s, 3H).

EXAMPLE 8

Preparation of 3-Hydroxy-4-{[5-hydroxy-3-methyl-1-(3-methylphenyl)-1H-pyrazol-4-yl]azo}benzoic Acid a) 1-(3-Methylphenyl)-3-phenyl-3-pyrazolin-5-one Following the procedure of Example 3b), except substituting 3-dimethylphenylhydrazine for 4-benzyloxyphenylhydrazine, the title compound was prepared (2.8 g; 90%). MS(ES) m/z 189 [M+H].

b) 3-Hydroxy-4-{[5-hydroxy-3-methyl-1-(3-methylphenyl)-1H-pyrazol-4-yl]azo}benzoic Acid Following the procedure of Example 1, except substituting 1-(3-methylphenyl)-3-methyl-3-pyrazolin-5-one for 3-methyl-1-(4-methylphenyl)-3-pyrazolin-5-one, the title compound was prepared as an orange solid (0.87 g; 50%). MS(ES) m/z 353 [M+H].

EXAMPLE 9

Preparation of 3-Hydroxy-4-{[5-hydroxy-3-methyl-1-(4-trifluoromethylphenyl)-1H-pyrazol-4-yl]azo}benzoic Acid a) 3-Phenyl-1-(4-trifluoromethylphenyl)-3-pyrazolin-5-one Following the procedure of Example 3b), except substituting 4-trifluoromethylphenylhydrazine for 4-benzyloxyphenylhydrazine, the title compound was prepared (3.3 g; 92%). MS(ES) m/z 243 [M+H].

b) 3-Hydroxy-4-{[5-hydroxy-3-methyl-1-(4-trifluoromethylphenyl)-1H-pyrazol-4-yl]azo}benzoic Acid Following the procedure of Example 1, except substituting 3-phenyl-1-(4-trifluoromethylphenyl)-3-pyrazolin-5-one for 3-methyl-1-(4-methylphenyl)-3-pyrazolin-5-one, the title compound was prepared as an orange solid (0.86 g g; 35%). MS(ES) m/z 407 [M+H].

EXAMPLE 10

Preparation of 3-{[1-(3,4-Dimethylphenyl)-5-hydroxy-3-methyl-1H-pyrazol-4-yl]azo}-2-hydroxybenzoic Acid Following the procedure of Example 1, except substituting 1-(3,4-dimethylphenyl)-3-methyl-3-pyrazolin-5-one for 3-methyl-1-(4-methylphenyl)-3-pyrazolin-5-one and 3-amino-2-hydroxybenzoic acid for 4-amino-3-hydroxybenzoic acid, the title compound was prepared as an orange solid (0.40 g, 32%). $^1$H NMR (400 MHz, d6-DMSO) δ 7.83 (m, 2H), 7.59 (d, J=7.8 Hz, 1H), 7.50 (d, J=7.8 Hz, 1H), 7.09 (d, J=8.0Hz, 1H), 6.60 (t, J=7.8 Hz, 1H), 2.29 (s, 3H), 2,24 (s, 3H), 2.21 (s, 3H).

EXAMPLE 11

Preparation of 5-Chloro-3-{[1-(3,4-dimethylphenyl)-5-hydroxy-3-methyl-1H-pyrazol-4-yl]azo}-2-hydroxybenzenesulfonic Acid Following the procedure of Example 1, except substituting 1-(3,4-dimethylphenyl)-3-methyl-3-pyrazolin-5-one for 3-methyl-1-(4-methylphenyl)-3-pyrazolin-5-one and 3-amino-5-chloro-2-hydroxybenzenesulfonic acid for 4-amino-3-hydroxybenzoic acid, the title compound was prepared as a red solid (0.74 g, 34%). mp 240° C. (decomp). MS(ES) m/z 437, 435 [M–H].

EXAMPLE 12

Preparation of 4-{[3-tert-Butyl-1-(3,4-dimethylphenyl)-5-hydroxy-1H-pyrazol-4-yl]azo}-3-hydroxybenzoic Acid a) 3-tert-Butyl-1-(3,4-dimethylphenyl)-3-pyrazolin-5-one Following the procedure of Example 3b), except substituting 3,4-dimethylphenylhydrazine for 4-benzyloxyphenylhydrazine and ethyl tert-butylacetate for ethyl acetoacetate, the title compound was prepared (25.1 g; 99%). MS(ES) m/z 245 [M+H].

b) 4-{[3-tert-Butyl-1-(3,4-dimethylphenyl)-5-hydroxy-1H-pyrazol-4-yl]azo}-3-hydroxybenzoic Acid Following the procedure of Example 1, except substituting 3-tert-butyl-1-(3,4-dimethylphenyl)-3-pyrazolin-5-one for 3-methyl-1-(4-methylphenyl)-3-pyrazolin-5-one, the title compound was prepared (0.71 g; 70%) as an orange solid, MS(ES) m/z 409 [M+H].

EXAMPLE 13

Preparation of 4-{[1-(3,4-Dimethylphenyl)-5-hydroxy-3-phenyl-1H-pyrazol-4-yl]azo}-3-hydroxybenzoic Acid a) 1-(3,4-Dimethylphenyl)-3-phenyl-3-pyrazolin-5-one Following the procedure of Example 3b), except substituting 3,4-dimethylphenylhydrazine for 4-benzyloxyphenylhydrazine and ethyl benzoylacetate for ethyl acetoacetate, the title compound was prepared (16.0 g; 61%). MS(ES) m/z 265 [M+H].

b) 4-{[1-(3,4-Dimethylphenyl)-5-hydroxy-3-phenyl-1H-pyrazol-4-yl]azo}-3-hydroxybenzoic Acid Following the procedure of Example 1, except substituting 1-(3,4-dimethylphenyl)-3-phenyl-3-pyrazolin-5-one for 3-methyl-1-(4-methylphenyl)-3-pyrazolin-5-one, the title compound was prepared (1.0 g; 78%) as a red solid, MS(ES) m/z 429 [M+H].

EXAMPLE 14

Preparation of methyl 4-{[5-Hydroxy-3-methyl-1-(4-methylphenyl)-1H-pyrazol-4-yl]azo}-3-hydroxybenzoate Following the procedure of Example 1, except substituting 1-(3,4-dimethylphenyl)-3-methyl-3-pyrazolin-5-one for 3-methyl-1-(4-methylphenyl)-3-pyrazolin-5-one and methyl 4-amino-3-hydroxybenzoate for 4-amino-3-hydroxybenzoic acid, the title compound was prepared as a red solid (0.059 g, 10%). MS(ES) m/z 367 [M+H].

EXAMPLE 15

Preparation of 4-{[1-(4-tert-Butylphenyl)-5-hydroxy-3-methyl-1H-pyrazol-4-yl]azo}-3-hydroxybenzoate Following the procedure of Example 1, except substituting 1-(4-tert-butylphenyl)-3-methyl-3-pyrazolin-5-one for 3-methyl-1-(4-methylphenyl)3-pyrazolin-5-one, the title compound was prepared as an orange solid (0.895 g, 45%). MS(ES) m/z 395 [M+H], Anal. ($C_{21}H_{22}N_4O_4$) calcd: C, 63.95; H, 5.62; N, 14.20 found: C, 63.65; H, 5.75; N, 13.83.

EXAMPLE 16

Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
|---|---|
| 3-hydroxy-4-{[5-hydroxy-3-methyl-1-(4-methylphenyl)-1H-pyrazol-4-yl]azo}benzoic acid (Compound 1) | 25 mg |
| Lactose | 55 mg |
| Talc | 16 mg |
| Magnesium Stearate | 4 mg |

EXAMPLE 17

Injectable Parenteral Composition

An injectable form for administering a presently invented agonist of the TPO receptor is produced by stirring 1.5% by weight of 4-{[1-(4-benzyloxyphenyl)-5-hydroxy-3-methyl-1H-pyrazol-4-yl]azo}-3-hydroxybenzoic acid, monosodium salt (Compound 2) in 10% by volume propylene glycol in water.

EXAMPLE 18

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
|---|---|
| 4-{[1-(3,4-dimethylphenyl)-5-hydroxy-3-methyl-1H-pyrazol-4-yl]azo}-3-hydroxybenzoic acid (Compound 6) | 20 mg |
| calcium sulfate dihydrate | 30 mg |
| sucrose | 4 mg |
| starch | 2 mg |
| talc | 1 mg |
| stearic acid | 0.5 mg |

Preferred among the compounds of the present invention are the following;

3-hydroxy-4-{[5-hydroxy-3-methyl-1-(4-methylphenyl)-1H-pyrazol-4-yl]azo}benzoic acid;

4-{[1-(4-benzyloxyphenyl)-5-hydroxy-3-methyl-1H-pyrazol-4-yl]azo}-3-hydroxybenzoic acid;

4-{[1-(4-tert-butylphenyl)-5-hydroxy-3-methyl-1H-pyrazol-4-yl]azo}-3-hydroxybenzoic acid;

3-{[-(3,4-dimethylphenyl)-5-hydroxy-3-methyl-1H-pyrazol-4-yl]azo}-2-hydroxybenzoic acid; and 4-{[1-(3,4-dimethylphenyl)-5-hydroxy-3-methyl-1H-pyrazol-4-yl]azo}-3-hydroxybenzoic acid.

The compound 4-{[1-(3,4-dimethylphenyl)-5-hydroxy-3-methyl-1H-pyrazol-4-yl]azo}-3-hydroxybenzoic acid demonstrated an activity of, EC50=1.8 uM, 50% TPO in the above luciferase assay.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating of thrombocytopenia in a mammal in need thereof which comprises administering to such mammal a therapeutically effective amount of a compound of Formula (II)

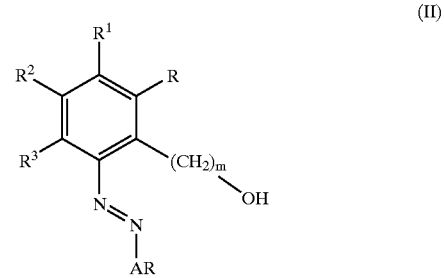

(II)

wherein:

R, $R^1$, $R^2$ and $R^3$ are each independently selected from hydrogen, $C_{1-6}$alkyl, $C_{1-6}$alkoxy, —$(CH_2)_pOR^4$, —$C(O)OR^4$, nitro, cyano, halogen, aryl, —$S(O)_nR^4$, cycloalkyl, protected —OH, —$CONR^5R^6$, —$NR^5R^6$, phosphonic acid, sulfonic acid, phosphinic acid and —$SO_2NR^5R^6$, where p is 0–6;

n is 0–2;

$R^4$ is hydrogen, alkyl, cycloalkyl, $C_1$–$C_{12}$aryl, substituted alkyl, substituted cycloalkyl and substituted $C_1$–$C_{12}$aryl and $R^5$ and $R^6$ are each independently selected from hydrogen, alkyl, $C_{3-6}$cycloalkyl, aryl or $R^5$ and $R^6$ taken together with the nitrogen to which they are attached represent a 5 to 6 member saturated ring containing up to one other heteroatom selected from oxygen and nitrogen;

m is 0–6; and

AR is cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, aryl, substituted cycloalkyl, substituted aryl, aryloxy, hydroxy, alkoxy, cycloalkyl, acyloxy, amino, N-acylamino, nitro, cyano, halogen, —C(O)OR$^4$, —C(O)NR$^7$R$^8$, —S(O)$_2$NR$^7$R$^8$, —S(O)$_n$R$^4$, protected —OH and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR$^4$, —C(O)NR$^7$R$^8$, —S(O)$_2$NR$^7$R$^8$, —S(O)$_n$R$^4$, aryloxy, nitro, cyano, halogen, and protected —OH, where R$^4$ is hydrogen, alkyl, cycloalkyl, C$_1$–C$_{12}$aryl, substituted alkyl, substituted cycloalkyl and substituted C$_1$–C$_{12}$aryl; and R$^7$ and R$^8$ are independently hydrogen, cycloalkyl, C$_1$–C$_{12}$aryl, substituted cycloalkyl, substituted C$_1$–C$_{12}$aryl, alkyl or alkyl substituted with one or more substituents selected from the group consisting of: alkoxy, acyloxy, aryloxy, amino, N-acylamino, oxo, hydroxy, —C(O)OR$^4$, —S(O)$_n$R$^4$, —C(O)NR$^4$R$^4$, —S(O)$_2$NR$^4$R$^4$, nitro, cyano, cycloalkyl, substituted cycloalkyl, halogen, C$_1$–C$_{12}$aryl, substituted C$_1$–C$_{12}$aryl and protected —OH, or R$^7$ and R$^8$ taken together with the nitrogen to which they are attached represent a 5 to 6 member saturated ring containing up to one other heteroatom selected from oxygen and nitrogen, where R$^4$ is as described above and n is 0–2; and pharmaceutically acceptable salts, hydrates, solvates and esters thereof.

2. The method of claim 1 wherein the mammal is a human.

3. The method of claim 2 wherein the compound is selected from 3-hydroxy-4-{[5-hydroxy-3-methyl-1-(4-methylphenyl)-1H-pyrazol-4-yl]azo}benzoic acid;

3-hydroxy-4-[(5-hydroxy-3-methyl-1-phenyl-1H-pyrazol-4-yl)azo]benzoic acid;

4-{[1-(4-benzyloxyphenyl)-5-hydroxy-3-methyl-1H-pyrazol-4-yl]azo}-3-hydroxybenzoic acid;

4-{[1-(4-chlorophenyl)-5-hydroxy-3-methyl-1H-pyrazol-4-yl]azo}-3-hydroxybenzoic acid;

4-{[1-(3-chlorophenyl)-5-hydroxy-3-methyl-1H-pyrazol-4-yl]azo}-3-hydroxybenzoic acid;

4-{[1-(3,4-dimethylphenyl)-5-hydroxy-3-methyl-1H-pyrazol-4-yl]azo}-3-hydroxybenzoic acid;

3-{[1-(3,4-dimethylphenyl)-5-hydroxy-3-methyl-1H-pyrazol-4-yl]azo}-4-hydroxybenzoic acid;

3-hydroxy-4-{[5-hydroxy-3-methyl-1-(3-methylphenyl)-1H-pyrazol-4-yl]azo}benzoic acid;

3-hydroxy-4-{[5-hydroxy-3-methyl-1-(4-trifluoromethylphenyl)-1H-pyrazol-4-yl]azo}benzoic acid;

3-{[1-(3,4-dimethylphenyl)-5-hydroxy-3-methyl-1H-pyrazol-4-yl]azo}-2-hydroxybenzoic acid;

2-{[1-(3,4-dimethylphenyl)-5-hydroxy-3-methyl-1H-pyrazol-4-yl]azo}-3-hydroxybenzoic acid;

5-chloro-3-{[1-(3,4-dimethylphenyl)-5-hydroxy-3-methyl-1H-pyrazol-4-yl]azo}-2-hydroxybenzenesulfonic acid;

3-tert-butyl-4-{[1-(3,4-dimethylphenyl)-5-hydroxy-1H-pyrazol-4-yl]azo}-3-hydroxybenzoic acid;

4-{[1-(3,4-dimethylphenyl)-5-hydroxy-3-phenyl-1H-pyrazol-4-yl]azo}-3-hydroxybenzoic acid;

methyl 3-hydroxy-4-{[5-hydroxy-3-methyl-1-(4-methylphenyl)-1H-pyrazol-4-yl]azo}benzoate; and 4-{[1-(4-tert-butylphenyl)-5-hydroxy-3-methyl-1H-pyrazol-4-yl]azo}-3-hydroxybenzoic acid;

and pharmaceutically acceptable salts, hydrates, solvates and esters thereof.

4. A method of enhancing platelet production in a mammal in need thereof which comprises administering to such mammal a therapeutically effective amount of a compound of claim 1.

5. The method of claim 4 wherein the mammal is a human.

6. The method of claim 5 wherein the compound is selected from 3-hydroxy-4-{[5-hydroxy-3-methyl-1-(4-methylphenyl)-1H-pyrazol-4-yl]azo}benzoic acid;

3-hydroxy-4-[(5-hydroxy-3-methyl-1-phenyl-1H-pyrazol-4-yl)azo]benzoic acid;

4-{[1-(4-benzyloxyphenyl)-5-hydroxy-3-methyl-1H-pyrazol-4-yl]azo}-3-hydroxybenzoic acid;

4-{[1-(4-chlorophenyl)-5-hydroxy-3-methyl-1H-pyrazol-4-yl]azo}-3-hydroxybenzoic acid;

4-{[1-(3-chlorophenyl)-5-hydroxy-3-methyl-1H-pyrazol-4-yl]azo}-3-hydroxybenzoic acid;

4-{[1-(3,4-dimethylphenyl)-5-hydroxy-3-methyl-1H-pyrazol-4-yl]azo}-3-hydroxybenzoic acid;

3-{[1-(3,4-dimethylphenyl)-5-hydroxy-3-methyl-1H-pyrazol-4-yl]azo}-4-hydroxybenzoic acid;

3-hydroxy-4-{[5-hydroxy-3-methyl-1-(3-methylphenyl)-1H-pyrazol-4-yl]azo}benzoic acid;

3-hydroxy-4-{[5-hydroxy-3-methyl-1-(4-trifluoromethylphenyl)-1H-pyrazol-4-yl]azo}benzoic acid;

3-{[1-(3,4-dimethylphenyl)-5-hydroxy-3-methyl-1H-pyrazol-4-yl]azo}-2-hydroxybenzoic acid;

2-{[1-(3,4-dimethylphenyl)-5-hydroxy-3-methyl-1H-pyrazol-4-yl]azo}-3-hydroxybenzoic acid;

5-chloro-3-{[1-(3,4-dimethylphenyl)-5-hydroxy-3-methyl-1H-pyrazol-4-yl]azo}-2-hydroxybenzenesulfonic acid;

3-tert-butyl-4-{[1-(3,4-dimethylphenyl)-5-hydroxy-1H-pyrazol-4-yl]azo}-3-hydroxybenzoic acid;

4-{[1-(3,4-dimethylphenyl)-5-hydroxy-3-phenyl-1H-pyrazol-4-yl]azo}-3-hydroxybenzoic acid;

methyl 3-hydroxy-4-{[5-hydroxy-3-methyl-1-(4-methylphenyl)-1H-pyrazol-4-yl]azo}benzoate; and 4-{[1-(4-tert-butylphenyl)-5-hydroxy-3-methyl-1H-pyrazol-4-yl]azo}-3-hydroxybenzoic acid;

and pharmaceutically acceptable salts, hydrates, solvates and esters thereof.

7. A pharmaceutical composition for use in enhancing platelet production which comprises a compound of Formula (II), as described in claim 1, and a pharmaceutically acceptable carrier.

8. A method of activating the TPO receptor which comprises administrating a compound of Formula (II), as described in claim 1.

9. The method of claim 1 wherein the compound is administered orally.

10. The method of claim 1 wherein the compound is administered parenterally.

11. A method of agonizing the TPO receptor in a subject which comprises administering an effective amount of a compound of Formula (II), as described in claim 1.

12. A method of agonizing the TPO receptor in a subject which comprises administering an effective amount of a compound of as described in claim 3.

13. A compound represented by the following Formula (I)

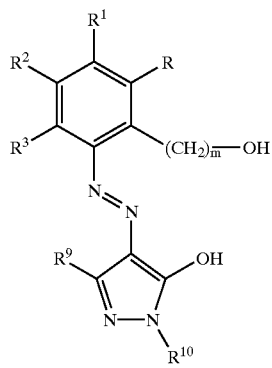

wherein:
R, $R^1$, $R^2$, $R^3$ and $R^9$ are each independently selected from hydrogen, $C_{1-6}$alkyl, $C_{1-6}$alkoxy, $-(CH_2)_pOR^4$, $-C(O)OR^4$, nitro, cyano, halogen, aryl, $-S(O)_nR^4$, cycloalkyl, protected $-OH$, $-CONR^5R^6$, phosphonic acid, sulfonic acid, phosphinic acid and $-SO_2NR^5R^6$, where
p is 0–6;
n is 0–2;
$R^4$ is hydrogen, alkyl, cycloalkyl, $C_1-C_{12}$aryl, substituted alkyl, substituted cycloalkyl and substituted $C_1-C_{12}$aryl, and
$R^5$ and $R^6$ are each independently selected from hydrogen, alkyl, $C_{3-6}$cycloalkyl, aryl or $R^5$ and $R^6$ taken together with the nitrogen to which they are attached represent a 5 to 6 member saturated ring containing up to one other heteroatom selected from oxygen and nitrogen;
m is 0–6; and
$R^{10}$ is a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, cycloalkyl, substituted cycloalkyl, aryl, substituted aryl, aryloxy, alkoxy, acyloxy, amino, nitro, cyano, halogen, hydroxy, protected $-OH$, and alkyl substituted with one or more substituents selected from the group consisting of: alkoxy, acyloxy, aryl, substituted aryl, cycloalkyl, substituted cycloalkyl, aryloxy, amino, nitro, cyano, halogen, hydroxy, and protected $-OH$; and pharmaceutically acceptable salts, hydrates, solvates and esters thereof;

provided that:

at least one of R, $R^1$, $R^2$ and $R^3$ is: sulfonic acid, $-C(O)OR^4$, tetrazole, $-CONR^5R^6$, phosphonic acid or phosphinic acid; where $R^4$, $R^5$ and $R^6$ are as described above;

and provided that:

when $R^1$ is carboxylic acid; R, $R^2$ and $R^3$ are hydrogen; and $R^9$ is methyl;

$R^{10}$ is not unsubstituted phenyl.

14. A compound of claim 13 selected from 3-hydroxy-4-{[5-hydroxy-3-methyl-1-(4-methylphenyl)-1H-pyrazol-4-yl]azo}benzoic acid;

4-{[1-(4-benzyloxyphenyl)-5-hydroxy-3-methyl-1H-pyrazol-4-yl]azo}-3-hydroxybenzoic acid;

4-{[1-(4-chlorophenyl)-5-hydroxy-3-methyl-1H-pyrazol-4-yl]azo}-3-hydroxybenzoic acid;

4-{[1-(3-chlorophenyl)-5-hydroxy-3-methyl-1H-pyrazol-4-yl]azo}-3-hydroxybenzoic acid;

4-{[1-(3,4-dimethylphenyl)-5-hydroxy-3-methyl-1H-pyrazol-4-yl]azo}-3-hydroxybenzoic acid;

3-{[1-(3,4-dimethylphenyl)-5-hydroxy-3-methyl-1H-pyrazol-4-yl]azo}-4-hydroxybenzoic acid;

3-hydroxy-4-{[5-hydroxy-3-methyl-1-(3-methylphenyl)-1H-pyrazol-4-yl]azo}benzoic acid;

3-hydroxy-4-{[5-hydroxy-3-methyl-1-(4-trifluoromethylphenyl)-1H-pyrazol-4-yl]azo}benzoic acid;

3-{[1-(3,4-dimethylphenyl)-5-hydroxy-3-methyl-1H-pyrazol-4-yl]azo}-2-hydroxybenzoic acid;

2-{[1-(3,4-dimethylphenyl)-5-hydroxy-3-methyl-1H-pyrazol-4-yl]azo}-3-hydroxybenzoic acid;

5-chloro-3-{[1-(3,4-dimethylphenyl)-5-hydroxy-3-methyl-1H-pyrazol-4-yl]azo}-2-hydroxybenzenesulfonic acid;

3-tert-butyl-4-{[1-(3,4-dimethylphenyl)-5-hydroxy-1H-pyrazol-4-yl]azo}-3-hydroxybenzoic acid;

4-{[1-(3,4-dimethylphenyl)-5-hydroxy-3-phenyl-1H-pyrazol-4-yl]azo}-3-hydroxybenzoic acid;

methyl 3-hydroxy-4-{[5-hydroxy-3-methyl-1-(4-methylphenyl)-1H-pyrazol-4-yl]azo}benzoate; and 4-{[1-(4-tert-butylphenyl)-5-hydroxy-3-methyl-1H-pyrazol-4-yl]azo}-3-hydroxybenzoic acid;

and pharmaceutically acceptable salts, hydrates, solvates and esters thereof.

15. A process for the preparation of a compound of Formula (I)

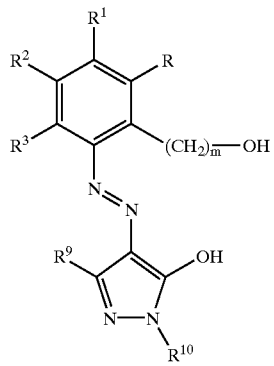
(I)

or a pharmaceutically acceptable salt, hydrate or solvate thereof, wherein R, $R^1$, $R^2$, $R^3$ $R^9$, $R^{10}$ and m are as described in claim 13, which comprises:

reacting a compound of the following formula (i),

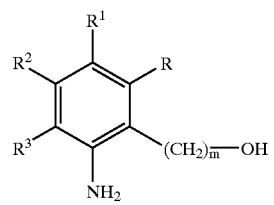
(i)

wherein R, $R^1$, $R^2$, $R^3$ and m are as described in claim 13 with a nitrite and an acid to form a diazonium compound of formula (ii),

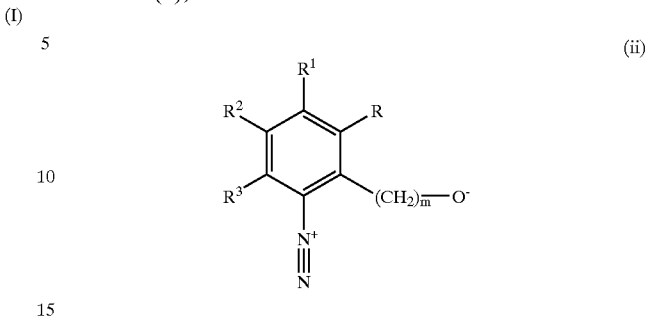
(ii)

wherein R, $R^1$, $R^2$, $R^3$ and m are as described in claim 13; followed by a coupling reaction with an appropriate pyrazole reactant, to form a compound of Formula (I), and thereafter optionally forming a pharmaceutically acceptable salt, hydrate or solvate thereof.

16. A process for preparing a pharmaceutical composition containing a pharmaceutically acceptable carrier or diluent and an effective amount of a compound of the Formula (II) as described in claim 1 and pharmaceutically acceptable salts, hydrates, solvates and esters thereof which process comprises bringing the compound of the Formula (II) into association with the pharmaceutically acceptable carrier or diluent.

* * * * *